United States Patent [19]

Adams et al.

[11] Patent Number: 5,135,004
[45] Date of Patent: Aug. 4, 1992

[54] IMPLANTABLE MYOCARDIAL ISCHEMIA MONITOR AND RELATED METHOD

[75] Inventors: John M. Adams, Issaquah; Clifton A. Alferness, Redmond, both of Wash.

[73] Assignee: InControl, Inc., Redmond, Wash.

[21] Appl. No.: 667,819

[22] Filed: Mar. 12, 1991

[51] Int. Cl.⁵ .............................................. A61B 5/04
[52] U.S. Cl. .................................... 128/696; 128/704
[58] Field of Search .............. 128/696, 702, 704, 705, 128/419 PG, 419 D

[56] References Cited

U.S. PATENT DOCUMENTS

| | | | |
|---|---|---|---|
| 4,210,149 | 7/1980 | Hellman et al. | 128/419 D |
| 4,223,678 | 9/1980 | Langer et al. | 128/419 D |
| 4,250,888 | 2/1981 | Grosskopf | 128/702 |
| 4,481,950 | 11/1984 | Duggan | 128/419 PT |
| 4,546,776 | 10/1985 | Bellin et al. | 128/704 |
| 4,562,846 | 1/1986 | Cox et al. | 128/696 |
| 4,586,508 | 5/1986 | Batina et al. | 128/419 |
| 4,625,730 | 12/1986 | Fountain et al. | 128/419 D |
| 4,679,144 | 7/1987 | Cox et al. | 128/702 |
| 4,681,117 | 7/1987 | Brodman et al. | 128/642 |
| 5,058,597 | 10/1991 | Onoda et al. | 128/708 |

OTHER PUBLICATIONS

"Localization of Regional Myocardial Ischemia by Recording of Monophasic Action Potentials," Franz et al., *Circulation,* vol. 69, No. 3, Mar., 1984, pp. 593-604.
"Precordial and Epicardial Surface Potentials During Myocardial Ischemia in the Pig," Holland et al., *Circulation Research,* vol. 37, Oct., 1975, pp. 471-480.
"Value of the Intracoronary Electrocardiogram to Monitor Myocardial Ischemia During Percutaneous Transluminal Coronary Angioplasty," Friedman et al., *Circulation,* vol. 74, No. 2, Aug., 1986, pp. 330-339.
"Relationship Between ST-Segment Elevation and Local Tissue Flow During Myocardial Ischemia in Dogs," Lekven et al., *Cardiovascular Research,* 1975, 9, pp. 627-633.

*Primary Examiner*—William E. Kamm
*Assistant Examiner*—Kennedy J. Schaetzle
*Attorney, Agent, or Firm*—Foley & Lardner

[57] ABSTRACT

An implantable device assists in the diagnosis of myocardial ischemia of a human heart and includes a plurality of electrodes and a like plurality of sense amplifiers for generating an electrogram for each of the electrodes. A digital to analog converter reads the voltage magnitudes of the electrogram ST segments which are then stored in a memory. An implantable receiver/transmitter is arranged to transmit the magnitudes of the electrogram ST segments to a nonimplanted external receiver.

31 Claims, 2 Drawing Sheets

IMPLANTABLE MYOCARDIAL ISCHEMIA MONITOR AND RELATED METHOD

BACKGROUND OF THE INVENTION

The present invention generally relates to an apparatus and method for assisting in the diagnosis of myocardial ischemia of a human heart. The present invention is more particularly directed to an apparatus and method for providing data related to the activity of the human heart, wherein the apparatus is fully implantable beneath the skin of a patient and wherein the data provided may be utilized to advantage for determining the presence or absence of ischemia in the human heart.

Patients who suffer what is commonly called a heart attack most often experience an episode of myocardial infarction. Myocardial infarction is a necrosis of cardiac tissue brought on by a reduction in blood flow to the infarcted area caused by either an obstruction in an artery or a thrombus in the artery. Patients who have suffered from myocardial infarction are generally treated with drugs or surgery to open the artery or undergo coronary artery bypass graft surgery to bypass the artery section having the obstruction or thrombus.

Each of the above-mentioned therapeutic techniques is effective in reestablishing blood flow through the effected artery. However, for each therapy, there is a percentage of patients that experience restenosis (reclosure of the artery) after therapy. Restenosis is largely an unpredictable event and the time required for the reclosure to occur may range from a matter of hours to years.

To monitor patients who have suffered from myocardial infarction, physicians may rely upon periodic ECGs (electrocardiograms) which generally require as many as ten leads to be attached to the patient. In addition, after the ECG, physicians then generally require the patient to take a stress test wherein the patient is caused to run on a tread mill until the patient is essentially exhausted to stress the heart. During and after the tread mill exercise the twelve lead is used to determine if the heart continues to receive adequate blood supply while under the stress conditions. Obviously such monitoring is inconvenient to the patient. Physicians may also rely upon Holtor monitoring recordings which may last from 24 to 48 hours. These additional monitoring techniques are equally as inconvenient and in addition, are also annoying. Since all of these monitoring techniques can only be administered periodically at best as a practical matter, and because restenosis and thus future episodes of myocardial infarction are unpredictable events, all too often, a restenosis problem is not detected until the patient experiences pain or suffers an episode of myocardial infarction. Unfortunately, research has shown that pain is not a reliable indicator of ischemia.

From the foregoing, it can been seen that there is a need in the art for a new and improved monitor and method for monitoring patients who have suffered myocardial ischemia and thus may have a potential restenosis problem. The present invention provides such an apparatus and method because the apparatus is fully implantable beneath the skin of the patient and includes electrodes which are arranged to make electrical contact with the heart by, for example, being attached to or near the heart and to monitor heart activity in the form of an electrogram for each electrode. More particularly, the monitor of the present invention, monitors the electrogram from specific areas of the heart and more specifically, a predetermined electrogram parameter at each such area which has been shown to be reliable for indicating ischemia in the human heart. The apparatus is arranged to store the electrogram data for retrieval by the physician periodically and upon request by the physician through a command made by an external transmitter. As a result, the physician is provided with an early warning monitoring system of the state of the circulation in the patient's coronary arteries. As will be seen hereinafter, if the ischemia exceeds a predetermined limit, the apparatus provides the patient with a detectable alert signal informing the patient that the patient should consult his or her physician.

SUMMARY OF THE INVENTION

The present invention therefore provides an apparatus for assisting in the diagnosis of myocardial ischemia of a human heart. The apparatus is fully implantable beneath the skin of a patient and includes at least one electrode being implantable beneath the skin of a patient and arranged for establishing electrical contact with the heart. The apparatus further includes sensing means implantable beneath the skin of a patient and being coupled to the at least one electrode for generating an electrogram representative of the activity of the heart at the at least on electrode and wherein the electrogram includes ST segments having voltage magnitudes. The apparatus further includes read means implantable beneath the skin of a patient for reading the voltage magnitudes of the electrogram ST segments, memory means implantable beneath the skin of a patient and coupled to the read means for storing the voltage magnitudes of the electrogram ST segments and communication means implantable beneath the skin of a patient and coupled to the memory means for transmitting the magnitudes of the electrogram ST segments to a nonimplanted external receiver.

The apparatus may further include a microprocessor arranged to determine the difference between the sensed ST segment voltages and a base line voltage and to activate an alarm means when the absolute magnitude of one of the differences exceeds a commanded limit. The microprocessor may further be arranged to cause an ST segment voltage to be stored in the memory means only when the absolute magnitude of its corresponding difference exceeds a commanded limit.

The present invention further provides a method for providing data for use in diagnosing myocardial ischemia of a human heart. The method includes the steps of providing at least one electrode, implanting the at least one electrode beneath the skin of a patient, establishing electrical contact between the at least one electrode and the heart of the patient, providing sensing means implanted beneath the skin of the patient coupled to the at least one electrode and generating an electrogram representative of the activity of the heart at the at least one electrode, wherein the electrogram includes ST segments. The method further includes the steps of providing voltage read means implanted beneath the skin of the patient, reading the voltage magnitudes of the electrogram ST segments, providing memory means implanted beneath the skin of the patient coupled to the voltage read means, storing the voltage magnitudes of the electrogram ST segments in the memory means, providing communication means implanted beneath the skin of the patient coupled to the memory means, and transmitting the magnitudes of the electrogram ST segments to a nonimplanted external receiver.

The present invention still further provides a method of providing data for use in diagnosing myocardial ischemia of a human heart. The method includes the steps of providing a plurality of electrodes, implanting the electrodes beneath the skin of a patient, and establishing electrical contact between the electrodes and respective different regions of the heart of the patient. The method further includes the steps of providing sensing means implanted beneath the skin of the patient coupled to the electrodes, and generating an electrogram for each electrode representative of the activity of the heart at each of the electrodes with electrogram including ST segments. The method further includes the steps of providing voltage read means implanted beneath the skin of the patient, reading the voltage magnitudes of the ST segments of each of the electrograms, providing memory means implanted beneath the skin of the patient coupled to the voltage read means, and storing the voltage magnitudes of the ST segments of each electrogram in said memory means. The method also includes the steps of providing communication means implanted beneath the skin of the patient coupled to the memory means, and transmitting the magnitudes of the electrogram ST segments to a nonimplanted external receiver.

BRIEF DESCRIPTION OF DRAWINGS

The features of the present invention which are believed to be novel are set forth with particularity in the appended claims. The invention, together with further objects and advantages thereof, may best be understood by making reference to the following description taken in conjunction with the accompanying drawings, and the several figures of which like reference numerals identify identical elements, and wherein:

DESCRIPTION OF THE PREFERRED EMBODIMENT

Figure 1:
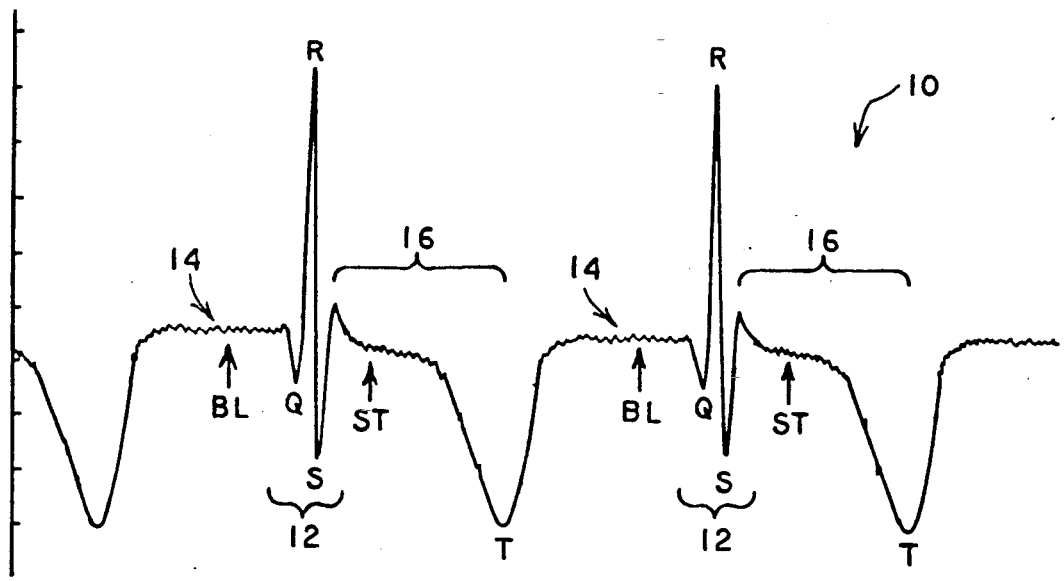
FIG. 1 illustrates a representative electrogram of a healthy human heart.

Referring now to FIG. 1, it illustrates an electrogram 10 representative of the electrical activity of a healthy heart. As will be noted, the electrogram 10 includes a QRS complex 12 which is preceded by a base line 14 and which is followed by an ST segment 16. As will also be noted from the electrogram 10, the voltage magnitude (ST) of the ST segment 16 is approximately equal to the voltage magnitude (BL) of the base line section 14 in the healthy heart.

Figure 2:
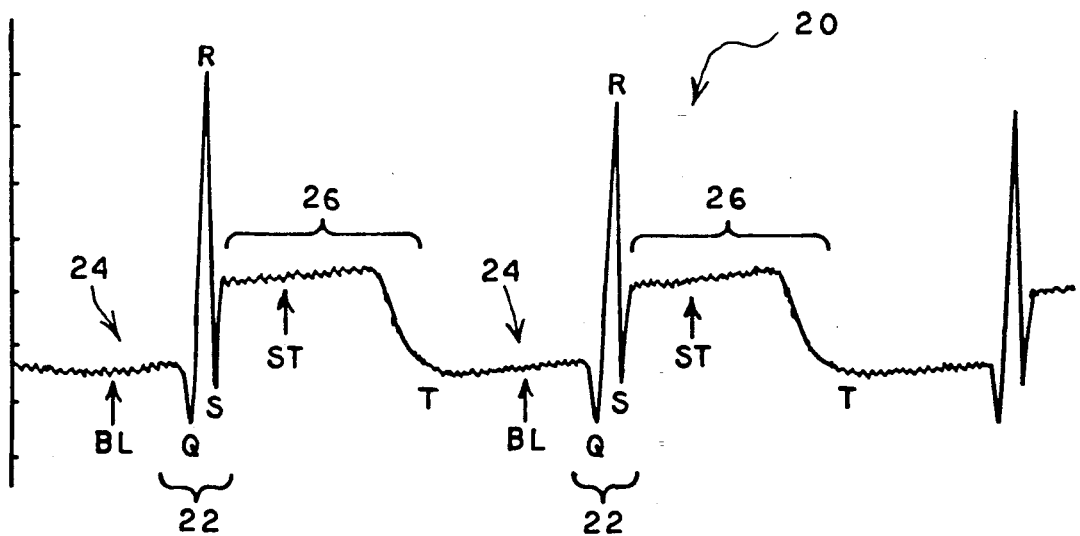
FIG. 2 illustrates a representative electrogram of a human heart suffering from ischemia.

Referring now to FIG. 2, it illustrates a representative electrogram 20 of a human heart suffering from ischemia. The electrogram 20 like the electrogram 10 includes a QRS complex 22 which is preceded by a base line 24 and which is followed by an ST segment 26. As can be noted from FIG. 2, the magnitude (ST) of the ST segment voltage is greater than the magnitude (BL) of the voltage of the base line 24. The difference between the voltage of the base line 24 and the voltage of the S segment 26 is referred to in the art as the ST segment voltage shift.

The ST segment voltage shift may be either in a positive or a negative direction depending upon the type of electrode used (bipolar or unipolar) and the position of the electrode relative to the ischemic tissue. As indicated in FIG. 2, the voltage shift is in the positive direction which will normally result with unipolar electrodes. Hence, human hearts suffering from ischemia may have either a negative or positive shift detected in the ST segment voltage. As a result, the absolute magnitude or value of the difference between the base line voltage and the voltage of the ST segment is considered to be a reliable indicator of potential ischemia in the human heart and, for example, a predetermined limit difference or shift of approximately five millivolts may be considered to indicate a condition of ischemia in the human heart. As will be seen hereinafter, the ischemia monitor of the present invention reads the voltage magnitude of the ST segment following the QRS complex.

Figure 3:
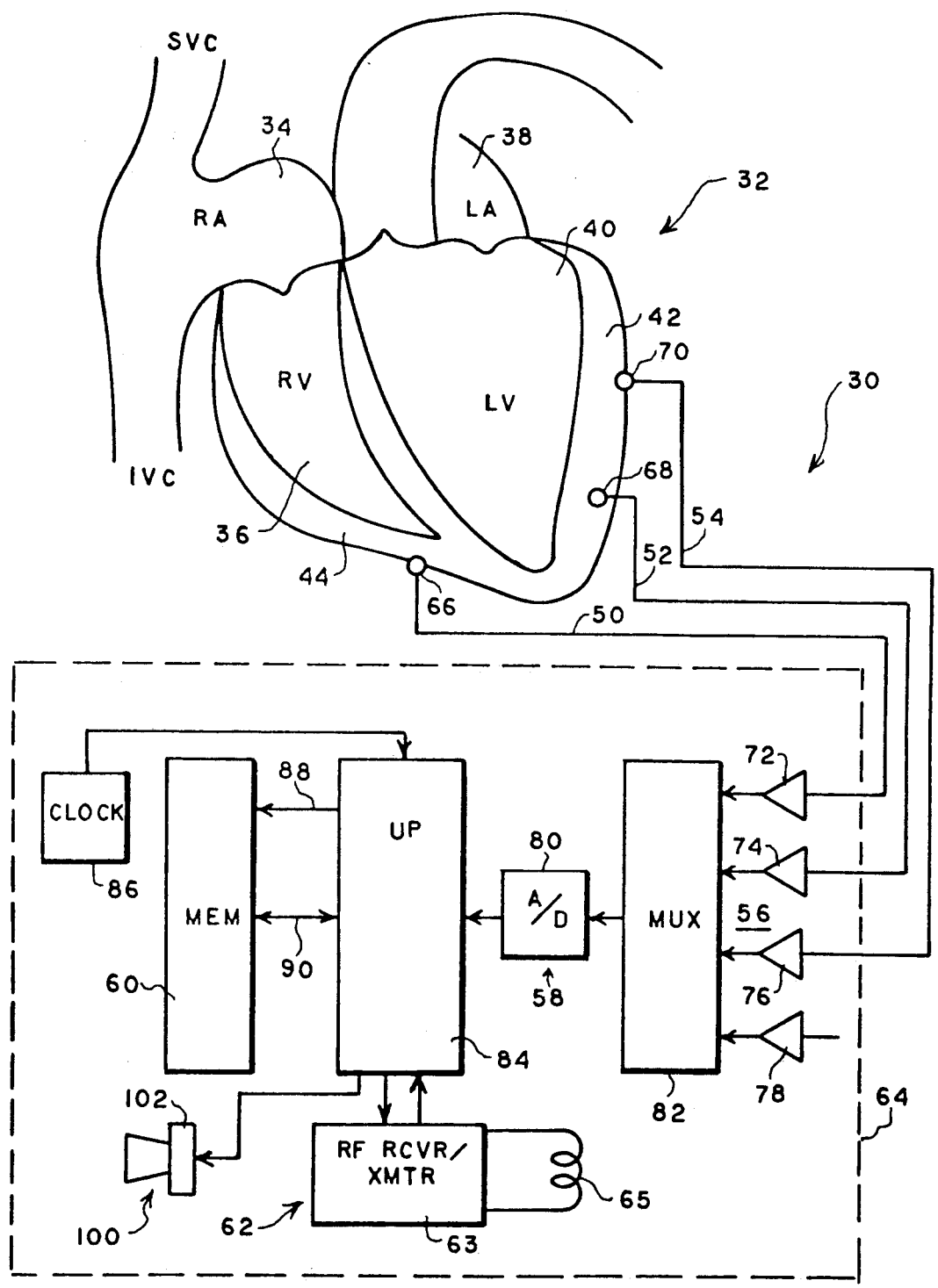
FIG. 3 is a schematic block diagram of a fully implantable apparatus embodying the present invention for assisting in the diagnosis of myocardial ischemia of a human heart and which is shown in association with a human heart in need of monitoring for ischemia.

Referring now to FIG. 3, it illustrates an ischemia monitor 30 embodying the present invention shown in association with a schematically represented human heart 32 in need of monitoring for myocardial ischemia. The heart 32 illustrated in FIG. 3 is shown to generally include a right atria 34, a right ventricle 36, a left atria 38, and a left ventricle 40. The right ventricle 36 and left ventricle 40 are shown in cross section to reveal myocardium regions 42 and 44 which may possibly suffer from ischemia.

The apparatus 30 generally includes a plurality of electrodes 50, 52, and 54, a sensing means 56, a read means 58, a memory 60, and communication means 62. All of the components of the apparatus 30 are contained within a common inclosure indicated by the dashed line 64 except for those portions of electrodes 50, 52, and 54 which extend outside of the common inclosure 64.

The electrodes 50, 52, and 54, as illustrated in FIG. 3, are epicardial electrodes and are thus arranged to be attached to the outer surface of the heart 32 in the region of the myocardium 42 and 44. Preferably, if the location of the region of potential myocardial ischemia is known, it is preferred to place the electrodes 50, 52, and 54 over or near each myocardial infarction or ischemic region where restenosis is considered to be most likely to occur. Such regions would be, for example, where grafts were made during coronary artery bypass graft surgery, for example. The electrodes 50, 52, and 54 are unipolar electrodes having poles 66, 68, and 70 respectively. The poles 66, 68, and 70 are placed into electrical contact with the heart by either being placed directly on the heart or to tissue near the heart for picking up electrical activity such as electrical activations within the heart 32.

The sensing means 56 comprises a plurality of sense amplifiers 72, 74, 76, and 78 with sense amplifiers 72, 74, and 76 having inputs coupled to the electrodes 50, 52, and 54. Although three electrodes are illustrated in the figure, it is contemplated by the present invention that a fewer or greater number of electrodes may be utilized without departing from the present invention. As a result, an electrogram is generated for each of the electrodes with each electrogram independently representing the activity of the heart 32 at each respective electrode pole and hence at each respective region of the heart being monitored.

The read means 58 is preferably an analog to digital converter 80 which is coupled to the outputs of the sense amplifiers 72, 74, 76, and 78 one at a time by a multiplexer 82. The analog to digital converter 80 reads the electrocardiogram voltages relative to a reference voltage such as the voltage of enclosure 64 and converts the electrocardiogram voltages to multiple-bit words in parallel-bit format. The multiple-bit representations of the electrogram voltages are processed by a microprocessor 84.

As will be noted in FIG. 3, the microprocessor 84 is coupled to a clock source 86 and to the multiplexer 82. The microprocessor is also coupled to the memory 60 by a multiple-bit address bus 88 and a bi-directional multiple-bit data bus 90. The address bus 88 permits the microprocessor 84 to address desired memory locations within the memory 60 for executing write or read operations. During a write operation, the microprocessor stores data in the memory 60 at the addresses defined by the multiple-bit addresses conveyed over bus 88 and conveys the data to the memory 60 over the multiple-bit bus 90. During a read operation, the microprocessor 84 obtains data from the memory 60 from the storage locations identified by the multiple-bit addresses provided over bus 88 and receives the data from the memory 60 over the bi-directional bus 90.

The microprocessor 84 controls the reading of the electrogram voltages and the storing of data, such as the magnitudes of the ST segment voltages, in the memory 60. By being coupled to the clock 86 and to the multiplexer 82, the microprocessor 84 is able to select which one of the inputs of the multiplexer is to be coupled to the input of the analog to digital converter 80 and to synchronously store the data in the memory 60. The microprocessor samples the electrogram voltages provided by the sense amplifiers 72, 74, and 76 as digitized by the analog to digital converter 80 at a rapid rate and detects when the slope of the electrogram is either a rapid positive or negative slope which may be seen in the electrograms of FIGS. 1 and 2. Following the detected rapid positive or negative slope in the electrogram, the microprocessor then looks to obtain the ST segment voltage from the analog to digital converter 80 from each of the sense amplifiers 72, 74, and 76. Preferably, the microprocessor obtains the ST segment voltage a predetermined time after the QRS complex 22 is detected by the detection of the rapid positive or negative slope in the electrogram. Such a predetermined time may be, for example, 80 ms.

As an alternative to the configuration illustrated in FIG. 3, the inputs of multiplexer 82 may be coupled directly to the electrodes 50, 52, and 54 with the output of the multiplexer then being coupled to a single sense amplifier. This would have the benefit of lower power consumption and assuring the same amplifying gain being applied to each electrogram. However, this would also result in slower voltage sampling due to voltage settling times.

The communication means 62 includes a receiver/transmitter 63 and a transmitting coil 65. Such communication means are well known in the art and may be utilized for receiving commands from external to the implantable enclosure 64 and for transmitting data to a receiver external to the implanted enclosure 64. One such communication system is disclosed, for example, in U.S. Pat. No. 4,586,508. The receiver/transmitter is coupled to the microprocessor 84 for conveying commands to the microprocessor and for receiving data from the microprocessor which the microprocessor acquires from the memory 60.

The microprocessor in receiving commands from external to the implanted enclosure 64 may be provided with a predetermined voltage level of the patient, such as the base line voltage, by the physician. When the microprocessor identifies the ST segment voltage, it may then determine the difference between the ST segment voltage and the base line voltage. If the absolute magnitude of the resulting difference is greater than a predetermined limit which may also be provided from external to the enclosure 64 by the physician, the microprocessor then may cause either the ST segment voltage or the determined difference (ST segment shift) to be entered into the memory 60. Since not all measured data is entered, in this manner, memory space within memory 60 may be conserved for only ST segment readings which are considered important to the physician. Also, for the ST segment voltages or voltage differences entered into the memory 60, the microprocessor may time stamp each entry so that upon being read out by the physician, the physician will know when the significant events occurred.

The microprocessor may also be programmed to determine the base line voltage on its own. This may be accomplished by storing the base line voltages and then, after the detection of a QRS complex, accessing the memory for the base line voltage measured a second predetermined time before the QRS complex. Such a second predetermined time may be 80 ms. Once having determined the base line voltage and after having the corresponding ST segment voltage, the microprocessor can then calculate the absolute value of the ST segment voltage shift. As a further alternative, capacitive coupling may be utilized to force the base line voltage seen by the microprocessor to be zero volts.

For obtaining data from the implanted monitor 30, the physician requests the data from external to the enclosure 64. The command is detected by the receiver/transmitter 63 and then conveyed to the microprocessor. In response to receiving the external command, the microprocessor 84 addresses the memory 60 to obtain the data stored in the memory 60. The microprocessor then conveys the data to the receiver/transmitter 63 which then transmits the data to an external receiver for readout by the physician.

It will also be noted that in FIG. 3, the apparatus 30 includes an alert means 100 which is coupled to the microprocessor 84. The alert means 100 may be an audio transducer 102 or may be a mechanical transducer to provide a detectable alarm which may be detected by the patient. When at least one ST segment shift determined by the microprocessor 84 is above a preset limit, which may be programmed into the microprocessor 84 from external to the apparatus 30 by the physician, the microprocessor then may be arranged to cause the alert means 100 to provide an alarm to the patient to inform the patient that the patient should consult his or her physician. Alternatively, if less sensitivity is desired, the microprocessor 84 may be programmed to activate the alarm only after a predetermined plurality of ST segment shifts, as for example, five ST segment shifts, have exceeded the preset limit. As a result, the apparatus 30 is capable of alerting the patient to a potential myocardial infarction episode before one occurs.

While a particular embodiment of present invention has been shown and described, modifications may be made, and it is therefore intended to cover in the appended claims all such changes and modifications which fall within the true spirit and scope of the invention.

What is claimed is:

1. An apparatus for assisting in the diagnosis of myocardial ischemia of a human heart, said apparatus being fully implantable beneath the skin of a patient and comprising:
    at least one electrode, said electrode being implantable beneath the skin of a patient and arranged for establishing electrical contact with the heart;
    sensing means implantable beneath the skin of a patient, said sensing means being coupled to said at least one electrode for generating an electrogram representative of the activity of the heart at said at least one electrode, said electrogram including ST segments having voltage magnitudes;
    read means implantable beneath the skin of a patient for reading the voltage magnitudes of said electrogram ST segments;
    memory means implantable beneath the skin of a patient and coupled to said read means for storing the voltage magnitudes of said electrogram ST segments; and
    communication means implantable beneath the skin of a patient and coupled to said memory means for transmitting said magnitudes of said electrogram ST segments to a nonimplanted external receiver.

2. An apparatus as defined in claim 1 including a plurality of said electrodes and wherein said sensing means is arranged to generate an electrogram for each said electrode.

3. An apparatus as defined in claim 2 wherein said electrodes are arranged to be attached to the human heart.

4. An apparatus as defined in claim 1 wherein said read means comprises an analog to digital converter.

5. An apparatus as defined in claim 2 wherein said sensing means comprises a plurality of sense amplifiers, each said sense amplifier being coupled to a respective one of said electrodes.

6. An apparatus as defined in claim 5 further including a multiplexer having a plurality of inputs coupled to said sense amplifiers and an output coupled to said read means for coupling each of said sense amplifiers to said read means one at a time.

7. An apparatus as defined in claim 6 wherein said read means comprises an analog to digital converter.

8. An apparatus as defined in claim 1 wherein said sensing means, said read means, said memory means, and said communication means are enclosed within a common enclosure.

9. An apparatus as defined in claim 2 wherein said electrodes are unipolar electrodes.

10. An apparatus as defined in claim 1 further including a microprocessor coupled between said read means and said memory means for controlling the reading of said electrogram ST segment voltages and the storing of said ST segment voltage magnitudes in said memory means.

11. An apparatus as defined in claim 10 wherein said microprocessor is coupled between said memory means and said communication means.

12. An apparatus as defined in claim 11 wherein said communication means is arranged for receiving commands from an external source.

13. An apparatus as defined in claim 12 wherein said microprocessor is arranged to determine the difference between said sensed ST segment voltages and a base line voltage and to activate said alarm means when the absolute magnitude of at least one of said differences exceeds a commanded limit.

14. An apparatus as defined in claim 13 wherein said microprocessor is arranged to determine the difference between said sensed ST segment voltage and said base line voltage and to cause an ST segment voltage magnitude to be stored in said memory means only when the absolute magnitude of its corresponding difference exceeds a commanded limit.

15. An apparatus as defined in claim 14 wherein said microprocessor is further arranged to provide a time stamp for each ST segment voltage magnitude entered into said memory means.

16. A method of providing data for use in diagnosing myocardial ischemia of a human heart, said method including the steps of:
    providing at least one electrode;
    implanting said electrode beneath the skin of a patient;
    establishing electrical contact between said electrode and the heart of the patient;
    providing sensing means implanted beneath the skin of the patient coupled to said electrode;
    generating an electrogram for said electrode representative of the activity of the heart at said electrode, said electrogram including ST segments;
    providing voltage read means implanted beneath the skin of the patient;
    reading the voltage magnitudes of said electrogram ST segments;
    providing memory means implanted beneath the skin of the patient coupled to said voltage read means;
    storing the voltage magnitudes of said electrogram ST segments in said memory means;
    providing communication means implanted beneath the skin of the patient coupled to said memory means; and
    transmitting said magnitudes of said electrogram ST segments to a nonimplanted external receiver.

17. A method as defined in claim 16 wherein said electrode is an epicardial electrode.

18. A method as defined in claim 16 wherein said sensing means is formed of at least one sense amplifier, said at least one sense amplifier being coupled to said at least one electrode.

19. A method as defined in claim 18 further including the step of converting said ST segment voltages from analog form to digital form.

20. A method as defined in claim 19 further including the step of synchronizing the reading of said electrogram ST segment voltages and the storing of said ST segment voltage magnitudes in said memory means.

21. A method as defined in claim 16 including the further steps of determining the difference between said sensed ST segment voltages and a base line voltage and providing an alarm when the absolute magnitude of at least one of said differences exceeds a predetermined limit.

22. A method as defined in claim 16 including the further steps of determining the difference between each sensed ST segment voltage and a base line voltage and storing a sensed ST segment voltage magnitude in said memory only when the absolute magnitude of its corresponding difference exceeds a predetermined limit.

23. A method as defined in claim 22 including the further step of time stamping each stored ST segment voltage entry.

24. A method of providing data for use in diagnosing myocardial ischemia of a human heart, said method including the steps of:
   providing a plurality of electrodes;
   implanting said electrodes beneath the skin of a patient;
   establishing electrical contact between said electrodes and respective different regions of the heart of the patient;
   providing sensing means implanted beneath the skin of the patient coupled to said electrodes;
   generating an electrogram for each said electrode representative of the activity of the heart at each said electrode, each said electrogram including ST segments;
   providing voltage read means implanted beneath the skin of the patient;
   reading the voltage magnitudes of said ST segments of each of said electrograms;
   providing memory means implanted beneath the skin of the patient coupled to said voltage read means;
   storing the voltage magnitudes of said ST segments of each said electrogram in said memory means;
   providing communication means implanted beneath the skin of the patient coupled to said memory means; and
   transmitting said magnitudes of said electrogram ST segments to a nonimplanted external receiver.

25. A method as defined in claim 24 wherein said electrodes are epicardial electrodes.

26. A method as defined in claim 24 wherein said sensing means is formed of a plurality of sense amplifiers, each said sense amplifier being coupled to a respective one of said electrodes.

27. A method as defined in claim 24 further including the step of converting said ST segment voltages from analog form to digital form.

28. A method as defined in claim 24 further including the step of synchronizing the reading of said electrogram ST segment voltages and the storing of said ST segment voltage magnitudes in said memory means.

29. A method as defined in claim 24 including the further steps of determining the difference between said sensed ST segment voltages and a base line voltage and providing an alarm when the absolute magnitude of at least one of said differences exceeds a predetermined limit.

30. A method as defined in claim 24 including the further steps of determining the difference between each sensed ST segment voltage and a base line voltage and storing a sensed ST segment voltage magnitude in said memory only when the absolute magnitude of its corresponding difference exceeds a predetermined limit.

31. A method as defined in claim 30 including the further step of time stamping each stored ST segment voltage entry.

* * * * *